United States Patent
Ishida et al.

(10) Patent No.: US 7,196,052 B2
(45) Date of Patent: Mar. 27, 2007

(54) FRAGRANCE COMPOSITION

(75) Inventors: Kenya Ishida, Hiratsuka (JP); Kenji Arata, Hiratsuka (JP); Kenji Maruyama, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 366 days.

(21) Appl. No.: 10/369,520

(22) Filed: Feb. 21, 2003

(65) Prior Publication Data
US 2003/0216283 A1 Nov. 20, 2003

(30) Foreign Application Priority Data
Feb. 22, 2002 (JP) .................... P. 2002-045985

(51) Int. Cl.
*A61K 8/18* (2006.01)
(52) U.S. Cl. ...................................... 512/25
(58) Field of Classification Search .................. 512/25
See application file for complete search history.

(56) References Cited

U.S. PATENT DOCUMENTS

| | | | | |
|---|---|---|---|---|
| 4,224,311 A | * | 9/1980 | Vanlerberghe et al. | 424/59 |
| 4,425,329 A | * | 1/1984 | Tsutsumi et al. | 514/772 |
| 4,486,406 A | * | 12/1984 | Abe et al. | 424/70.28 |
| 4,487,760 A | * | 12/1984 | Yamamoto et al. | 424/70.1 |
| 4,570,648 A | * | 2/1986 | Schenk | 131/276 |

FOREIGN PATENT DOCUMENTS

| | | | |
|---|---|---|---|
| DE | 2645282 | * | 12/1979 |
| JP | 4-337395 A | | 11/1992 |
| JP | 5-295388 A | | 11/1993 |
| JP | 7-62383 A | | 3/1995 |
| JP | 2001-40395 A | | 2/2001 |
| JP | 2001-49291 A | | 2/2001 |
| JP | 2002155296 | * | 5/2002 |

\* cited by examiner

*Primary Examiner*—Monique T. Cole
(74) *Attorney, Agent, or Firm*—Sughrue Mion, PLLC

(57) ABSTRACT

A fragrance composition having high fragrance properties such as fragrance diffusivity and long-lasting property obtained without changing the fragrance note of the fragrance composition which is useful in various fragrance providing products such as cosmetics, toiletry products, bath compositions and pharmaceuticals having satisfactory fragrance properties such as fragrance diffusivity and long-lasting property. The fragrance composition contains 0.1 to 90% by weight of a glyceryl ether derivative represented by the following general formula (I), such as 2-ethylhexyloxypropanediol as a fixative or fragrance note-improving agent. The fragrance-providing product contains 0.01 to 50% by weight of the fragrance composition in the final product composition. General formula (I) is:

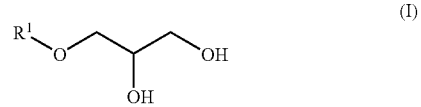

(I)

wherein $R^1$ represents an aliphatic hydrocarbon group having 4 to 12 carbon atoms which may have a branched chain or an aromatic hydrocarbon group, which may have a substituent.

4 Claims, No Drawings

FRAGRANCE COMPOSITION

FIELD OF THE INVENTION

The present invention relates to a fragrance composition. More specifically, it relates to a fragrance composition excellent in fragrance properties such as fragrance diffusivity and long-lasting property of fragrance as well as a fixative effect, and various products such as a cosmetic, toiletry product, bath composition and pharmaceutical containing the same.

BACKGROUND OF THE INVENTION

Hitherto, during preparation of an excellent fragrance composition by blending aroma substances, various fixatives or fragrance note-improving agents which adjust the fragrance properties and fixative property of aroma substances have been incorporated into a fragrance for the purpose of maintaining the desired aroma. As such fixatives or fragrance note-improving agents, there have been specifically proposed and employed dipropylene glycol, triethyl citrate, benzyl benzoate, benzyl salicylate, diethyl phthalate, isopropyl myristate, and the like. Of these, it has been reported that benzyl salicylate induces delayed contact dermatitis ("Hifu (Skin)", Vol. 23, No. 4, pp. 421–441), and hence the compound is not preferable in view of safety. Moreover, diethyl phthalate is not preferable because its use is voluntarily restrained as an endocrine disturbing chemical. Some other fixatives exhibit only a low effect of imparting a long-lasting property of fragrance and the fragrance of the fixatives themselves sometimes modulates the fragrance note of a fragrance composition in an undesirable direction, so that it has been desired to develop an odorless fragrance note-improving agent which can impart an excellent fragrance-lasting property which also does not modulate the fragrance note of a fragrance composition.

Under such circumstances, various fixatives and fragrance note-improving agents have been proposed in order to satisfy such demands. For example, there have been proposed p-menthane-3,8-diol in JP-A-4-337395, 2-hydroxymethyl-cycloalkanol derivatives in JP-A-5-295388, specific biphenyl-compounds in JP-A-7-62383, and so forth, as fixatives. However, these compounds have hardly satisfied the requirements of versatility, fixative effect and the like as fixatives.

In addition, with regard to the above fixatives and fragrance note-improving agents, the effects thereof as blended fragrances by sensory evaluation on a blotter are described, but the effects in products provided with the blended fragrances are not described. Thus, it has been desired to develop a blended fragrance and a fragrance note-improving agent which provides an excellent fragrance note-improving effect in final products.

SUMMARY OF THE INVENTION

Accordingly, the present invention aims at improving fragrance properties and the long-lasting property of a fragrance composition and also providing products in which the improved effects are seen. That is, more specifically, the present invention aims at providing a fragrance note-improving agent having high fragrance properties such as fragrance diffusivity and long-lasting property and a high fixative property without changing the fragrance note of the base fragrance composition, and a fragrance composition containing the same, and furthermore it aims at providing various products having satisfactory fragrance properties such as fragrance diffusivity and long-lasting property and a satisfactory fixative property.

As a result of intensive studies for solving the above problems, the present inventors found that a glyceryl ether derivative represented by the following general formula (I) remarkably enhances fragrance diffusivity and long-lasting property of a fragrance composition, and reached the present invention.

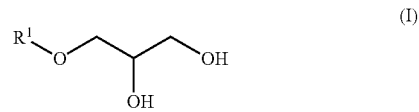

(I)

wherein $R^1$ represents an aliphatic hydrocarbon group having 4 to 12 carbon atoms which may have a branched chain or an aromatic hydrocarbon group which may have a substituent.

The present invention also relates to the fragrance composition which contains 0.1 to 90% by weight of the glyceryl ether derivative represented by the above general formula (I) based on the total weight of the fragrance composition.

Moreover, the present invention further relates to a cosmetic, toiletry product, bath composition or pharmaceutical, wherein 0.01 to 50% by weight of the above fragrance composition based on the total weight of the final product is incorporated into a final product.

The present invention also relates to a method for forming a fragrance composition which comprises adding a starting fragrance composition a glyceryl ether derivative: represented by the above general formula (I) in an amount effective to improve the fragrance properties such as the fragrance diffusivity and the long-lasting property of the final fragrance composition and to form final products in which such improved effects are seen, which method comprises adding the final fragrance a composition comprising 0.1 to 90% by weight of a glyceryl ether derivative represented by general formula (I) in an amount effective to improve the above fragrance properties in the final products, which amount will provide from 0.01 to 50% by weight of the fragrance composition in the final product based on the total weight of the final product, and wherein the final product is a cosmetic, a toiletry, a food or drink, a detergent, a softener, a bath composition, a pharmaceutical, and the like.

DETAILED DESCRIPTION OF THE INVENTION

The present invention provides:

(1) a fragrance composition comprising 0.1 to 90% by weight of a glyceryl ether derivative represented by the general formula:

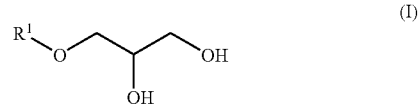

(I)

wherein $R^1$ represents an aliphatic hydrocarbon group having 4 to 12 carbon atoms which may have a branched chain or an aromatic hydrocarbon group, which aromatic hydrocarbon group may have a substituent;

(2) the fragrance composition according to (1) above, wherein $R^1$ in the above general formula (I) is an aliphatic hydrocarbon group having 5 to 10 carbon atoms;

(3) the fragrance composition according to (2) above, wherein $R^1$ in the above general formula (I) is a 2-ethylhexyl group;

(4) a cosmetic, toiletry product, bath composition or pharmaceutical, wherein 0.01 to 50% by weight of the fragrance composition according to (1), (2) or (3) above is incorporated into the final product composition;

(5) a fragrance composition comprising a glyceryl ether derivative as described in (1) above and at least one fragrance substance selected from the group consisting of ketones, aldehydes, esters, alcohols, ethers, terpenes, natural essential oils, synthetic musks, and other commonly used fragrance substances;

(6) a fragrance composition as described in (5) above, wherein the fragrance substance is at least one carbonyl compound selected from the group consisting of methyl dihydrojasmonate, 10-oxa-16-hexadecanolide, styrallyl acetate, linalyl acetate, ethyl 2,2,6-trimethylcyclohexane carboxylate and hexamethylhexahydrocyclopentabenzopyran; and (7) a cosmetic, a toiletry, a food or drink, a detergent, a softener, a bath composition, or a pharmaceutical, which respectively comprises the fragrance composition of claim (6).

The following will explain the present invention in detail.

The glyceryl ether derivative represented by the above general formula (I) for use in the present invention is a compound wherein $R^1$ represents an aliphatic hydrocarbon group having 4 to 12 carbon atoms which may have a branched chain or an aromatic hydrocarbon group which may have a substituent.

Illustrative examples of the saturated straight-chain hydrocarbon groups of $R^1$ include n-butyl, n-hexyl, n-octyl, n-nonyl, n-decyl, n-undecyl, n-dodecyl, and the like. Illustrative examples of the branched hydrocarbon groups of $R^1$ include iso-butyl, sec-butyl, tert-butyl, 3-methylbutyl, 4-methylpentyl, 5-methylhexyl, 2-ethylhexyl, 3,5,5-trimethylhexyl, 6-methylpentyl, 7-methyloctyl, 8-methylnonyl, 2,6-dimethylheptyl, 3,7-dimethyloctyl, and the like. Illustrative examples of the unsaturated straight-chain hydrocarbon groups of $R^1$ include 1-butenyl, 2-butenyl, 3-butenyl, 4-pentenyl, 5-hexenyl, 6-heptenyl, 7-octenyl, 8-nonenyl, 9-decenyl, 1-pentenyl, 1-hexenyl-1-heptenyl, 1-octenyl, 1-nonenyl, 1-decenyl, 9-octadecenyl, and the like. Illustrative examples of the-unsaturated hydrocarbon group which may have a branched chain of $R^1$ include 2-methyl-1-propenyl, 3-methyl-2-butenyl, 4-methyl-3-pentenyl, 5-methyl-4-hexenyl, 6-methyl-5-heptenyl, 7-methyl-6-octenyl, 8-methyl-7-nonenyl, 1-methyl-1-propenyl, 1-methyl-1-butenyl, 1-methyl-1-pentenyl, 1-methyl-1-hexenyl, 1-methyl-1-heptenyl, 1-methyl-1-octenyl, 1-methyl-1-nonenyl, 2,6-dimethyl-5-heptenyl, 2,6-dimethyl-1-heptenyl, and the like. Illustrative examples of the aromatic hydrocarbon group which may have a substituent include phenyl, 2-methylphenyl, 4-methylphenyl, 2,4,6-trimethylphenyl, 4-tert-butylphenyl, and the like.

$R^1$ is preferably an aliphatic hydrocarbon group having 5 to 10 carbon atoms which also has a branched chain.

Illustrative examples the preferable $R_1$ include n-hexyl, n-octyl, n-nonyl, n-decyl, 3-methylbutyl, 4-methylpentyl, 5-methylhexyl, 2-ethylhexyl, 3,5,5-trimethylhexyl, 6-methylheptyl, 7-methyloctyl, 4-pentenyl, 5-hexenyl, 6-heptenyl, 7-octenyl, 8-nonenyl, 9-decenyl, 1-pentenyl, 1-hexenyl, 1-heptenyl, 1-octenyl, 1-nonenyl, 1-decenyl, 4-methyl-3-pentenyl, 5-methyl-4-hexenyl, 6-methyl-5-heptenyl, 7-methyl-6-octenyl, 8-methyl-7-nonenyl, 1-methyl-1-butenyl, 1-methyl-1-pentenyl 1-methyl-1-hexenyl, phenyl, 2-methylphenyl, 4-methylphenyl, and the like. 2-Ethylhexyl group is particularly preferable in view of the effects of the-invention and the like.

In the above formula, when the carbon number of the aliphatic hydrocarbon group of $R^1$ is less than 4, there arise problems that not only is the fixative effect low but also a change of the fragrance note of blended fragrances and products to which these blended fragrances are added frequently occurs due to the fragrance of the glyceryl ether itself. On the other hand, when the carbon number of the aliphatic hydrocarbon group is more than 12, there arise problems in that compatibility with a blended fragrance becomes low and fragrance diffusivity is lowered due to its solidification of the glyceryl ether at room temperature. Further, the fixative effect is low, which is not preferable. As the substituent of the aromatic hydrocarbon group, there is preferably an aliphatic hydrocarbon group which may be branched, more preferably a lower alkyl group such as a methyl group.

It is preferred in accordance with the present invention, that $R^1$ be the aliphatic hydrocarbon group as earlier defined and it is further preferred that when $R^1$ is the aromatic hydrocarbon group, the aromatic hydrocarbon group as a substituent.

Examples of the preferable glyceryl ether derivative represented by the above general formula (I) include 3-methylbutoxypropane-1,2-diol, n-hexyloxypropane-1,2-diol, n-octyloxypropane-1,2-diol, 2-ethylhexyloxypropane-1,2-diol, 3,5,5-trimethylhexyloxypropane-1,2-diol, n-decyloxypropane-1,2-diol, phenyloxypropane-1,2-diol, 2-methylphenyloxypropane-1,2-diol and 4-methylphenyloxypropane-1,2-diol, but the glyceryl ether derivative for use in the present invention is not limited thereto. In this connection, of these, 2-ethylhexyloxypropane-1,2-diol is particularly preferred in view of the effects provided thereby. The glyceryl ether derivative represented by the above general formula (I) can be employed solely or as a mixture of two or more of the derivatives. The incorporation of these glyceryl ether derivatives into known or well-known fragrance compositions enables a remarkable enhancement of fragrance diffusivity and long-lasting property of fragrance without changing the fragrance note. It thus becomes possible to obtain a fragrance composition having desired fragrance properties and fixative property.

The glyceryl ether derivatives represented by the above general formula (I) for used in the present invention are known compounds and can be obtained by production methods as described in JP-A-2001-49291, JP-A-2001-40395 or JP-A-47-16647, or JP-B-61-48813. Examples of these production methods include a method of reacting an alcohol and an epoxy compound such as an epohalohydrin or glycidol using an acid catalyst such as $BF_3$ or a compound represented by the general formula:

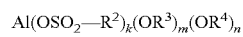

$$Al(OSO_2—R^2)_k(OR^3)_m(OR^4)_n$$

(wherein $R^2$ represents a hydrocarbon group which may have a substituent, $R^3$ and $R^4$ are the same or different and each represents a hydrocarbon group which may have a substituent, and k is a numerical figure of 1 to 3, m and n each is a numerical figure of 0 to 2 and k+m+n=3).

The glyceryl ether derivatives represented by the general formula (I) above for use in the present invention are colorless and nearly odorless oily substances, and are highly compatible with conventional fragrance compositions. These glyceryl ethers are known as detergent ingredients for liquid detergents having a high washing effect toward stubborn sebaceous soil such as soil at collars and cuffs and degenerated oil stain around kitchens (JP-A-2001-49291 and JP-A-2001-40395), but the capability of these ether derivative to enhance the fragrance property, fragrance diffusivity, and fixative effect of fragrance compositions has not been heretofore known or suspected.

The fragrance composition of the present invention contains the glyceryl ether derivative represented by the general formula (I) as an essential ingredient, but ketones, aldehydes, esters, alcohols, ethers, terpenes, natural essential oils, synthetic musk and the like, which are known or well-known as fragrance-blending ingredients, may be additionally incorporated singly or optionally as a combination of two or more of such materials, whereby a fragrance composition can be prepared.

Examples of the fragrance composition to which the glyceryl ether derivative represented by the general formula (I) is applied include fragrances as are commonly employed in various products such as external preparations including cosmetics and pharmaceuticals, detergents for bodies and cloths, bleaches, softeners and bath compositions.

The amount of the glyceryl ether derivative represented by the general formula (I) to be incorporated in a fragrance composition is suitably determined depending on the fragrance composition to which the derivative is added or the forms of the products to which the resulting fragrance composition itself further added and the methods of use thereof. In general, the amount is preferably from 0.1 to 90% by weight, more preferably 0.5 to 30% by weight relative to the total amount of the fragrance composition including the glyceryl ether derivative used. Moreover, with regard to a fragrance composition obtained according to the present invention, the amount to be incorporated into a final product and the method of using the same may be optionally changed depending on the kind of the product, the intended use, and the like. Usually, the amount of the fragrance composition to be incorporated into the final product is from 0.01 to 50% by weight, preferably 0.05 to 30% by weight, in the final product composition.

Examples of the products to which the fragrance composition of the present invention is applied include skin cosmetics, hair cosmetics such as shampoos, rinses, conditioners, hair tonics and hair creams, cosmetics such as scents, colognes, soaps, indoor aromatics and toothpastes, toiletry products such as detergents and softeners, pharmaceuticals such as bath compositions, cataplasms and ointments; however, products to which the fragrance composition of the present invention can be applied are not limited to the above.

Further, the amount of the fragrance composition incorporated into the products in each product case may be as follows in terms of the amount of the glyceryl ether derivative represented by the general formula (I). In the case of skin cosmetics, hair cosmetics such as shampoos, rinses, conditioners, hair tonics and hair creams, cosmetics such as scents, colognes and soaps, and bath compositions, it is usually preferable to use the fragrance composition in a concentration of 0.01 to 30% by weight, particularly 0.05 to 10% by weight, based on the total composition weight of each product. The amount of glycerin ether derivative to be incorporated in toiletry products such as detergents and softeners is usually preferably to a concentration of 0.01 to 1% by weight, particularly 0.05 to 0.3% by weight, based on the total composition weight of each product.

Optional ingredients may be suitably added to the product to which the fragrance composition is added depending on the intended use of each product, so that the product is a final product such as a cosmetic, toiletry product, bath composition, sanitary material, pharmaceutical, or the like.

The glyceryl ether derivative represented by the above general formula (I) is incorporated in the state that it is contained in a fragrance composition at its incorporation into a final product. As a consequence, a final product which is extraordinarily excellent in fragrance properties such as fragrance diffusivity and long-lasting property of the product and fixative property can be obtained as compared with the case that the glyceryl ether derivative and the fragrance composition are incorporated as separate ingredients, quite a surprising effect. Accordingly, the fragrance composition of the present invention is particularly preferable as a fragrance composition to be incorporated into a final product.

The fragrance composition of the present invention contains a glycerol ether derivative represented by formula (1) as an essential component and can further comprise other fragrance components commonly employed in the art in an appropriate combination, such as ketones, aldehydes, esters, alcohols, ethers, terpenes, natural essential oils, and synthetic musk.

In other words, the fragrances which can be used in the invention are not limited in kind and include those usually used in various products, such as preparations for external application (e.g., cosmetics and pharmaceuticals), cleansers for human body, clothes, and hard surfaces, bleachers, and softeners. Useful fragrances include synthetic ones and natural ones of animal or plant origin. Examples are hydrocarbons, such as aliphatic hydrocarbons, terpene hydrocarbons, and aromatic hydrocarbons; alcohols, such as aliphatic alcohols, terpene alcohols, and aromatic alcohols; ethers, such as aliphatic ethers and aromatic ethers; oxides, such as aliphatic oxides and terpene oxides, aldehydes, such as aliphatic aldehydes, terpene aldehydes, hydrogenated aromatic aldehydes, thioaldehydes, and aromatic aldehydes; ketones, such as aliphatic ketones, terpene ketones, hydrogenated aromatic ketones, cyclic ketones, and aromatic ketones; acetals, ketals, phenols, phenol ethers; acids, such as fatty acids, hydrogenated aromatic carboxylic acids, and aromatic carboxylic acids; acid amides; lactones, such as aliphatic lactones, macrocyclic lactones, terpene lactones, hydrogenated aromatic lactones and aromatic lactones; esters, such as aliphatic esters, furan carboxylic esters, alicyclic carboxylic esters, cyclohexylcarboxylic esters, terpene carboxylic esters, and aromatic carboxylic esters; and nitrogen-containing compounds, such as nitromusks, nitriles, amines, pyridines, quinolines, pyrrole, and indole. Typical fragrances useful in the invention are listed below.

C6–C12 Aldehydes, anisaldehyde, acetal R, acetophenone, acetylcedrene, adoxal, allylamyl glycolate, allyl cyclohexanepropionate, α-damascone, β-damascone, δ-damascone, ambrettolide, ambroxan, amylcinnamic aldehyde, amylcinnamic aldehyde dimethylacetal, amyl valerianate, amyl salicylate, isoamyl acetate, isoamyl salicylate, aurantiol, acetyl eugenol, bacdanol, benzyl acetate, benzyl alcohol, benzyl salicylate, bergamyl acetate, bornyl acetate, butyl butyrate, p-t-butylcyclohexanol, p-t-butylcyclohexyl acetate, o-t-butylcyclohexanol, benzaldehyde, benzyl formate, caryophyllene, cashmerane, carvone, cedramber, cedryl acetate, cedrol, celestolide, cinnamic alcohol, cinnamic aldehyde, cis-jasmone, citral, citral dimethyl acetal, citrasal, citronellal, citronellol, citronellyl acetate, citronellyl formate, citronellyl nitrile, cyclaset, cyclamen aldehyde, cyclaprop, caron, coumarin, cinnamyl acetate, δ-C6–C13 lactone, dimethylbenzylcarbinol, dihydrojasmon, dihydrolinalool, dihydromyrcenol, dimetol, dimyrcetol, diphenyl oxide, ethyl vanillin, eugenol, fruitate, fenchyl alcohol, phenylethyl phenylacetate, galaxolide, γ-C6–C13 lactone, geraniol, geranyl acetate, geranyl formate, geranyl nitrile, hedion, helional, heliotropin, cis-3-hexanol, cis-3-hexenyl acetate, cis-3-hexenyl salicylate, hexylcinnamic aldehyde, hexyl salicylate, hyacinth dimethyl acetal, hydrotropic alcohol, hydroxycitronellal, indole, ionone, isobornyl acetate, isocyclocitral, Iso E Super, isoeugenol, isononyl acetate, isobutylquinoline, jasmal, jamolactone, jasmopirane, corvone, ligustoral, lilial, lime oxide, limonene, linalool, linalool oxide, linalyl acetate, lyral, manzanate, myol, menthanyl acetate, menthonate, methyl anthranilate, methyl eugenol, menthol, α-methylionone, β-methylionone, γ-methylionone, methyl isoeugenol, methyl lavender ketone, methyl salicylate, muguet aldehyde, mugol, musk TM-II, musk 781, musk C14, musk T, musk ketone, musk tibetene, musk moskene, myrac aldehyde, methylphenyl acetate, nerol, neryl acetate, nopyl acetate, nopyl alcohol, neobergamate, oak moss No. 1, orivone, oxyphenylon, p-cresyl methyl ether, pentalide, phenylethyl alcohol, phenylethyl acetate, phenylacetaldehyde, dimethyl acetal, α-pinene, rubafuran, rosephenone, rose oxide, Sandalore, Sandela, Santalex, Santalinol, styralyl acetate, styralyl propionate, terpineol, terpinyl acetate, tetrahydrolinalool, tetrahydrolinalyl acetate, tetrahydrogeraniol, tetrahydrogeranyl acetate, tonalide, traseolide, tripral, thymol, vanillin, verdox, yara yara, anis oil, bay oil, bois de-rose oil, cananga oil, cardamon oil, cassia oil, cedarwood oil, orange oil, mandarin oil, tangerine oil, basil oil, nutmeg oil, citronella oil, clove oil, coriander oil, elemi oil, eucaryptus oil, fennel oil, galbanum oil, geranium oil, hiba oil, hinoki oil, jasmine oil, lavandin oil, lavender oil, lemon oil, lemonglass oil, lime oil, neroli oil, oak moss oil, ocotea oil, patchouli oil, peppermint oil, perilla oil, petitgrain oil, pine oil, rose roil, rosemary oil, camphor oil, ho leaf oil, clary sage oil, sandalwood oil, spearmint oil, spike lavender oil, star anis oil, thyme oil, tonka bean tincture, turpentine oil, vanilla bean tincture, vetiver oil, bergamot oil, ylang ylang oil, grapefruit oil, yuzu (Citrus Junos Tanaka) oil, benzoin, balsam peru, balsam tolu, tuberose oil, musk tincture, castrium tincture, civet tincture, and ambergris tincture.

The products to which the fragrance composition is applied may contain arbitrary components according to the use. Other components usually employed in dermatological preparations for external application, such as cosmetics and pharmaceuticals, can be incorporated appropriately according to necessity. Such components include powder components, fats and oils, waxes, hydrocarbons, higher fatty acids, higher alcohols, esters, silicones, anionic surfactants, cationic surfactants, amphoteric surfactants, nonionic surfactants, humectants, water-soluble polymers, thickeners, film-forming agents, UV absorbers, sequestering agents, lower alcohols, polyhydric alcohols, sugars, amino acids, organic amines, synthetic resin emulsions, pH adjustors, skin nourishing agents, vitamins, antioxidants, antioxidation assistants, fragrances, and water. Examples of components that can be compounded are listed below. The dermatological preparations of the invention are produced by compounding the above-described essential component with one or more components arbitrarily selected from the following in a usual manner.

The powder components include, but are not limited to, talc, kaolin, mica, magnesium carbonate, calcium carbonate, aluminum silicate, barium silicate, calcium silicate, magnesium silicate, strontium silicate, metal tungstates, magnesium, silica, zeolite, barium sulfate, calcined calcium sulfate (calcined gypsum), calcium phosphate, hydroxyapatite, ceramic powder, metal soaps (e.g., zinc myristate, calcium palmitate, and aluminum stearate); organic powders, such as polyamide resin powder (nylon powder), polyethylene powder, polymethyl methacrylate powder, polystyrene powder, styrene-acrylic acid copolymer resin powder, and cellulose powder; inorganic white pigments, such as titanium dioxide and zinc oxide; inorganic red pigments, such as iron oxide (rouge) and iron titanate; carbon black; inorganic purple pigments, such as Mango Violet and Cobalt Violet; inorganic green pigments, such as cobalt titanate; inorganic blue pigments, such as Ultramarine and Prussian Blue; pearly-pigments, such as titanium oxide-coated mica, titanium oxide-coated bismuth oxychloride, titanium oxide-coated talc, colored titanium oxide-coated mica, bismuth oxychloride, and argentine; metallic powder pigments, such as aluminum powder and copper powder; organic pigments, e.g., red Nos. 201, 202, 204, 205, 220, 226, 228, and 405, orange Nos. 203 and 204, yellow Nos. 205 and 401, and blue No. 404; zirconium, barium or aluminum lake organic pigments, e.g., red Nos. 3, 104, 106, 227, 230, 401, and 505, orange No. 205, yellow Nos. 4, 5, 202, and 203, green No. 3, and blue No. 1; and natural pigments, such as chlorophyll and β-carotene. Any other kinds of powders are useful as long as applicable to ordinary cosmetics.

The oils (liquid at room temperature) include avocado oil, camellia oil, turtle oil, macadamia nut oil, corn oil, mink oil, olive oil, rape seed oil, egg yolk oil, sesame oil, wheat germ oil, castor oil, linseed oil, safflower oil, cotton seed oil, soybean oil, peanut oil, tea seed oil, rice bran oil, jojoba oil, germ oil, triglycerol, glycerol trioctanoate, and glycerol triisopalminate.

The fats (solid at room temperature) include cacao butter, coconut oil, horse fat, hydrogenated coconut oil, palm oil, beef tallow, sheep tallow, hydrogenated beef tallow, palm kernel oil, lard, beef bone fat, Japan wax kernel oil, hydrogenated oils, neat's foot oil, Japan wax, and hydrogenated castor oil.

The waxes include beeswax, candelilla wax, cotton wax, carnauba wax, bayberry wax, mealybug wax, whale wax, lanolin, lanolin acetate, liquid lanolin, lanolin fatty acid isopropyl ester, hexyl laurate, reduced lanolin, jojoba wax, hard lanolin, POE (polyoxyethylene) lanolin alcohol ether, POE lanolin alcohol acetate, POE cholesterol ether, polyethylene glycol lanolin fatty acid ester, and POE hydrogenated lanolin alcohol ether.

The hydrocarbon oils include liquid paraffin, squalene, paraffin, squalene, and vaselin.

The higher fatty acids include lauric acid, myristic acid, palmitic acid, stearic acid, oleic acid, 12-hydroxystearic acid, undecylenic acid, tolic acid, isostearic acid, linoleic acid, linolenic acid, eicosapentaenoic acid (EPA), and docosahexaenoic acid (DHA).

The higher alcohols include straight-chain alcohols, such as lauryl alcohol, cetyl alcohol, stearyl alcohol, behenyl alcohol, myristyl alcohol, oleyl alcohol, and cetostearyl alcohol, and branched alcohols, such as glycerol monostearyl ether, 2-decyltetradecinol, lanolin alcohol, cholesterol, phytosterol, hexyldodecanol, isostearyl alcohol, and octyldodecanol.

Synthetic ester oils include isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexylate, dipentaerythritol fatty acid esters, neopentyl glycol dicaprinate, diisostearyl malate, glycerol di-2-heptylundecanoate, trimethylolpropane tri-2-ethylhexylate, trimethylolpropane triisostearate, pentaerythritol tetra-2-ethylhexylate, glycerol tri-2-ethylhexylate, trimethylolpropane triisostearate, cetyl 2-ethylhexanoate, 2-ethylhexyl palmitate, glycerol trimyristate, glycerol tri-2-heptylundecanoate, castor oil fatty acid methyl ester, oleic acid oil, cetostearyl alcohol, 2-heptylundecyl palmitate, diisobutyl adipate, 2-octyldodecyl N-lauryol-L-glutamate, di-2-heptylundecyl adipate, ethyl laurate, 2-hexyldecyl myristate, 2-hexyldecyl palmitate, 2-hexyldecyl adipate, diisopropyl sebacate, 2-ethylhexyl succinate, ethyl acetate, butyl acetate, amyl acetate, and triethyl citrate.

The silicones include acyclic polysiloxanes, such as dimethyl polysiloxane, methylphenyl polysiloxane, and methylhydrogen polysiloxane, alicyclic polysiloxanes, such as decamethyl polysiloxane, dodecamethyl polysiloxane, and tetramethyltetrahydrogen polysiloxane; silicone resins having a three-dimensional network structures: and silicone rubbers.

The anionic surfactants include fatty acid soaps, such as soap bases, sodium laurate, and sodium palmitate; higher alkylsulfuric ester salts, such as sodium laurylsulfate and potassium laurylsulfate; alkyl ether sulfuric ester salts, such as triethanolamine POE laurylsulfate and sodium POE laurylsulfate; N-acylsarcosinic acids, such as sodium lauroylsarconinate, higher fatty acid amidosulfonates, such as sodium N-myristoyl-N-methyltaurine, sodium palm oil fatty acid methyltauride, and sodium laurylmethyltauride; phosphoric ester salts, such as sodium POE oleyl ether phosphate and POE stearyl ether phosphate; sulfosuccinates, such as sodium di-2-ethylhexylsulfosuccinate, sodium POE monolauroylmonoethanolamide sulfosuccinate, and sodium lauryl polypropylene glycol sulfosuccinate; alkylbenzenesulfonates, such as sodium linear dodecylbenzenesulfonate, triethanolamine linear dodecylbenzenesulfonate, and linear dodecylbenzenesulfonic acid; N-acylglutamates, such as monosodium N-lauroylglutamate, disodium N-stearoylglutamate, monosodium N-myristoyl-L-glutamate; higher fatty acid ester sulfuric ester salts, such as sodium hydrogenated coconut oil fatty acid glycerol sulfate; sulfated oils, such as Turkey red oil; POE alkyl ether carboxylic acids, POE alkyl allyl, ether carboxylates, α-olefinsulfonates, higher fatty acid ester sulfonates, secondary alcohol sulfuric ester salts, higher fatty acid alkylolamide sulfuric ester salts, sodium lauroyl monoethanolamidesuccinate, ditriethanolamine N-palmitoylaspartate, and sodium casein.

The cationic surfactants include alkyltrimethylammonium salts, such as stearyltrimethylammonium chloride and lauryltrimethylammonium chloride; dialkyldimethylammonium salts, such as distearyldimethylammonium chloride, alkylpyridinium salts, such as poly-N,N'-dimethyl-3,5-methylenepiperidinium chloride and cetylpyridinium chloride; alkyl quaternary ammonium salts, alkyldimethylbenzylammonium salts, alkylisoquinolinium salts, dialkylmorpholinium salts, POE alkylamines, alkylamine salts, polyamine fatty acid derivatives, amyl alcohol fatty acid derivatives, benzalkonium chloride, and benzethonium chloride.

The amphoteric surfactants include imidazoline surfactants, such as sodium 2-undecyl-N,N,N-(hydroxyethylcarboxymethyl)-2-imidazoline and disodium 2-cocoyl-2-imidazolinium hydroxide-1-carboxyethyloxy; and betaines, such as 2-heptadecyl-N-carboxymethyl-N-hydroxyethylimidazolinium betaine, lauryldimethylaminoacetic acid betaine, alkyl betaines, amide betaines, and sulfobetaines.

Oleophilic nonionic surfactants include sorbitan fatty acid esters, such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, and diglycerol sorbitan tetra-2-ethylhexylate; glycerol or polyglycerol fatty acids esters, such as glycerol mono-cotton seed oil fatty acid ester, glycerol monoerucate, glycerol sesquioleate, glycerol monostearate, glycerol α,α'-oleate pyroglutamate, and glycerol monostearate malate; propylene glycol fatty acid esters, such as propylene glycol monostearate; hydrogenated castor oil derivatives, and glycerol alkyl ethers.

Hydrophilic nonionic surfactants include POE sorbitan fatty acid esters, such as POE sorbitan monooleate, POE sorbitan monostearate, POE sorbitan monooleate, and POE sorbitan tetraoleate; POE sorbitol fatty acid esters, such as POE sorbitol monolaurate, POE sorbitol monooleate, POE sorbitol pentaoleate, and POE sorbitol monostearate; POE glycerol fatty acid esters, such as POE glycerol monostearate, POE glycerol monoisostearate, and POE glycerol triisostearate; POE fatty acid esters, such as POE monooleate, POE distearate, POE monodioleate, and ethylene glycol distearate; POE alkyl ethers, such as POE lauryl ether, POE oleyl ether, POE stearyl ether, POE behenyl ether, POE-2-octyldodecyl ether, and POE-cholestanol ether; POE alkyl phenyl ethers, such as POE octyl phenyl ether, POE nonyl phenyl ether, and POE dinonylphenyl ether; Pluronic type surfactants, such as Pluronic; POE.POP alkyl ethers, such as POE.POP cetyl ether, POE.POP 2-decyltetradecyl ether, POE.POP monobutyl ether, POE.POP hydrogenated lanolin, and POE-POP glycerol ether; tetraPOE.tetraPOP ethylenediamine condensates, such as Tetronic; POE castor oil or hydrogenated castor oil derivatives, such as POE castor oil, POE hydrogenated castor oil, POE hydrogenated castor oil monoisostearate, POE hydrogenated castor oil triisostearate, POE hydrogenated castor oil monopyroglutamate monoisostearate, and POE hydrogenated castor oil maleate; POE beeswax lanolin derivatives, such as POE sorbitol beeswax; alkanolamides, such as coconut oil fatty acid diethanolamide, lauric acid monoethanolamide, and fatty acid isopropanolamides; POE propylene glycol fatty acid esters, POE alkylamines, POE fatty acid amides, sucrose fatty acid esters, POE nonylphenyl formaldehyde condensates, alkylethoxydimethylamine oxides, and trioleyl phosphate.

The humectants include polyethylene glycol, propylene glycol, glycerol, 1,3-butylene glycol, xylitol, sorbitol, maltitol, chondroitin sulfate, hyaluronic acid, mucoitin sulfate, cholesteryl 12-hydroxystearate, ceramids, glucosylceramids, sodium lactate, bile acid salts, dl-pyrrolidonecarboxylic acid salts, short-chain soluble collagen, diglycerol (EO) PO adducts, extract of chestnut rose (*R. roxburghii plena*), extract of yarrow (*Achillea milleofolium*), and extract of yellow sweetclover (*Melilotus officinalis*).

Natural water-soluble polymers include polymers of plant origin, such as gum arabic, tragacanth gum, galactan, carob gum, gum karaya, carrageenan, pectin, agar, quince seed, algae colloid (brown algae extract), starch (from rice, corn, potato or wheat), and glycyrrhizin; polymers of microorganism origin, such as xanthan gum, dextran, succinoglucan, and pullulan; and polymers of animal origin, such as collagen, casein, albumin, and gelatin.

Semisynthetic water-soluble polymers include starch polymers, such as carboxymethyl starch and methylhydroxypropyl starch; cellulosic polymers, such as methyl cellulose, nitro cellulose, ethyl cellulose, methylhydroxypropyl cellulose, hydroxyethyl cellulose, sodium cellulose sulfate, hydroxypropyl cellulose, sodium carboxymethyl cellulose (CMC), crystalline cellulose, and cellulose powder; and alginate polymers, such as sodium alginate and propylene glycol alginate.

Synthetic water-soluble polymers include vinyl polymers, such as polyvinyl alcohol, polyvinyl methyl ether, polyvinylpyrrolidone, and carboxyvinyl polymer (Carbopol); polyethylene oxides, such as polyethylene glycol 20,000, 4,000,000 or 600,000; ethylene oxide-propylene oxide copolymers, acrylic polymers, such as sodium polyacrylate, polyethyl acrylate and polyacrylamide; polyethylene-imine, and cationic polymers.

Inorganic water-soluble polymers include bentonite, aluminum magnesium silicate, Laponite, hectorite, and silicic anhydride.

The thickeners include gum arabic, carrageenan, gum karaya, tragacanth gum, carob gum, quince seed, casein, dextrin, gelatin, sodium pectate, sodium alginate, methyl cellulose, ethyl cellulose, hydroxyethyl cellulose, hydroxpropyl cellulose, sodium polyacrylate, carboxyvinyl polymer, dialkyldimethylammonium sulfate cellulose, xanthan gum, aluminum magnesium silicate, and bentonite.

The UV absorbers include benzoic acid UV-absorbers, such as p-aminobenzoic acid (hereinafter PABA), PABA monoglyceride, N,N-dipropoxy-PABA ethyl ester, N,N-diethoxy-PABA ethyl ester, N,N-dimethyl-PABA ethyl ester, N,N-dimethyl-PABA butyl ester, and N,N-dimethyl-PABA methyl ester; anthranilic acid UV absorbers, such as homomenthyl N-acetylanthranilate; salicylate UV absorbers, such as amyl salicylate, menthyl salicylate, homomenthyl salicylate, octyl salicylate, phenyl salicylate, benzyl salicylate, and p-isopropanolphenyl salicylate; cinnamate U absorbers, such as octyl cinnamate, ethyl 4-isopropylcinnamate-, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl p-methoxycinnamate, 2-ethylhexyl p-methoxycinnamate, 2-ethoxyethyl p-methoxycinnamate, cyclohexyl p-methoxycinnamate, ethyl α-cyano-β-phenylcinnamate, 2-ethylhexyl α-cyano-β-phenylcinnamate, and glycerol mono-2-ethylhexanoyl-di-p-methoxycinnamate; benzophenone UV absorbers, such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonates, 4-phenylbenzophenone, 2-ethylhexyl-4'-phenylbenzophenone-2-carboxylates, 2-hydroxy-4-n-octoxybenzophenone, and 4-hydroxy-3-carboxybenzophenone; 3-(4'-methylbenzylidene)-d,l-camphor, 3-benzylidene-d,l-camphor, urocanic acid, ethyl urocanate, 2-phenyl-5-methylbenzoxazole, 2,2'-hydroxy-5-methylphenylbenzotriazole, 2-(2'-hydroxy-5'-t-octylphenyl) benzotriazole, 2-(2'-hydroxy-5'-methylphenyl)benzotriazole, dizensalazine, dianisoylmethane, 4-methoxy-4'-t-butyldibenzoylmethane, and 5-(3,3-dimethyl-2-norbornylidene)-3-pentan-2-one.

The sequestering agents include 1-hydroxyethane-1,1-diphosphonic acid, tetrasodium 1-hydroxyethane-1,1-diphosphonate, disodium edetate, trisodium edetate, tetrasodium edetate, sodium citrate, sodium polyphosphate, sodium metaphosphate, gluconic acid, phosphoric acid, citric acid, ascorbic acid, succinic acid, and edetic acid.

The lower alcohols include methanol, ethanol, propanol, isopropyl alcohol, isobutyl alcohol, and t-butyl alcohol.

The polyhydric alcohols include dihydric alcohols, such as ethylene glycol, propylene glycol, trimethylene glycol, 1,2-butylene glycol, 1,3-butylene glycol, tetramethylene glycol, 2,3-butylene glycol, pentamethylene glycol, 2-butene-1,4-diol, hexylene glycol, and octylene glycol; trihydric alcohols, such as glycerol, trimethylolpropane, and 1,2,6-heanetriol; tetrahydric alcohols, such as pentaerythritol; pentahydric alcohols, such as xylitol, hexahydric alcohols, such as sorbitol and mannitol; polyhydric alcohols, such as diethylene glycol, dipropylene glycol, triethylene glycol, polypropylene glycol, tetraethylene glycol, diglycerol, polyethylene glycol, triglycerol, tetraglycerol, and polyglycerol; dihydric alcohol alkyl ethers, such as ethylene glycol monomethyl ether, ethylene glycol monoethyl ether, ethylene glycol monobutyl ether, ethylene glycol monophenyl ether, ethylene glycol monohexyl ether, ethylene glycol mono-2-methylhexyl ether, ethylene glycol isoamyl ether, ethylene glycol benzyl ether, ethylene glycol isopropyl ether, ethylene glycol: dimethyl ether, ethylene, glycol diethyl ether, and ethylene glycol dibutyl ether; dihydric alcohol alkyl ethers, such as diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methyl ethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, and dipropylene glycol butyl ether; dihydric alcohol ether esters, such as ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, and propylene glycol monophenyl ether acetate; glycerol monoalkyl ethers, such as chimyl alcohol, selachyl alcohol, and batyl alcohol; sugar alcohols, such as sorbitol, maltitol, maltotriose, mannitol, sucrose, erythritol, glucose, fructose, starch sugars, maltose, xylitose, and reduction products of starch sugars; Glysolid, tetrahydrofurfuryl alcohol, POE tetrahydrofurfuryl alcohol, POP butyl ether, POP-POE butyl ether, tripolyoxypropylene glycerol ether, POP glycerol ether, POP glycerol ether phosphate, and POP.POE pentaerythritol ether.

Monosaccharides include trioses, such as D-glycerylaldehyde and dihydroxyacetone; tetroses, such as D-erythrose, D-erythrulose, D-threose, and erythritol; pentoses, such as L-arabinose, D-xylose, L-lyxose, D-arabinose, D-ribose, D-riburose, D-xylulose, and L-xylulose; hexoses, such as D-glucose, D-talose, D-psicose, D-galactose, D-fructose, L-galactose, L-mannose, and D-tagatose; heptoses, such as aldoheptose, and heptulose; octoses, such as octulose; deoxysugars, such as 2-deoxy-D-ribose, 6-deoxy-L-galactose, and 6-deoxy-L-mannose; amino sugars, such as D-glucosamine, D-galactosamine, sialic acid, aminouronic acid, and muramic acid; and uronic acids, such as D-glucuronic acid, D-mannuronic acid, L-guluronic acid, D-galacturonic acid, and L-iduronic acid.

Oligosaccharides include sucrose, gentianose, umbelliferose, lactose, planteose, isolychnose, α,α-threhalose, raffinose, lychnose, umbilicin, stachyose, and verbascose.

Polysaccharides include cellulose, quince seed, chondroitin sulfate, starch, galactan, dermatan sulfate, glycogen, gum arabic, heparan sulfate, hyaluronic acid, tragacanth gum, chondroitin, xanthan gum, mucoitin sulfate, guar gum, dextran, and caronic acid.

The amino acids include neutral amino acids, such as glycine, alanine, valine, leucine, isoleucine, serine, threonine, tryptophan, cystine, cysteine, methionine, proline, and hydroxyproline; acidic amino acids, such as aspartic acid, glutamic acid, asparagine, and glutamine; and basic amino acids, such as alginine, histidine, lysine, and hydroxylysine.

Amino acid derivatives include sodium acyl sarcosinates (e.g., sodium lauroyl sarcosinate), acylglutamic acid salts, sodium acyl-β-alanine, glutathione, and pyrrolidonecarboxylic acid.

The organic amines include monoethanolamine, diethanolamine, triethanolamine, morpholine, triisopropanolamine, 2-amino-2-methyl-1,3-propanediol, and 2-amino-2-methyl-1-propanol.

The synthetic resin emulsions include acrylic resin emulsions, polyethyl acrylate emulsions, acrylic resin solutions, polyalkyl acrylate emulsions, and polyvinyl acetate emulsions.

The pH adjustors include buffers, such as lactic acid-sodium lactate and citric acid-sodium citrate. The vitamins include vitamins A, B1, B2, B6, E and their derivatives, pantothenic acid and its derivatives, and biotin.

The antioxidants include tocopherols, dibutylhydroxytoluene, butylhydroxyanisole, and gallic acid esters.

The antioxidation assistants include phosphoric acid, citric acid, ascorbic acid, maleic acid, malonic acid, succinic acid, fumaric acid, cephalin, hexametaphosphates, phytic acid, and ethylenediaminetetraacetic acid.

The dermatological preparation of the invention may have an arbitrary dose form. The essential component of the invention is compounded with one or more of the above-described optional components and formulated in a usual manner into any dose form fit for the intended product, such as a solution form, a solubilized form, an emulsion form, an oil form, a gel form, a powder dispersion form, a water/oil two-layer form, and a water/oil/powder three-layer form.

The following will illustrate the present invention with reference to Synthesis Example and Examples, but the present invention is by no means limited thereto.

SYNTHESIS EXAMPLE 1

(Synthesis of 3-methylbutoxypropane-1,2-diol)

3-Methylbutanol (158 g, 1.78 mol), aluminum triisopropoxide (3.61 g, 17.7 mmol) and p-phenolsulfonic acid (9.40 g, 54 mmol) were charged into a 1-liter reaction vessel and the whole was heated to 90° C. with stirring. After an additional. 1 hour of stirring under reduced pressure (266 hPa). The vessel was heated to 100° C. and epichlorohydrin (170 g, 1.78 mol) was added dropwise thereto over a period of 30 minutes, followed by an additional 3 hours of stirring. The reaction mixture was kept at a 50° C. and 50% sodium hydroxide aqueous solution (285 g, 3.56 mol) was added dropwise thereto over a period of 1 hour. After an additional 3 hours of stirring, 400 ml of water was added to the mixture and the mixture was allowed to separate into layers. After removal of the water layer, 100 ml of toluene was added to the oil layer and the resulting solution was washed with 300 ml of 5% brine three times and concentrated to obtain a crude reaction product (218 g). Distillation of the product gave 3-methylbutyl glycidyl ether (150 g) (bp: 63–64° C./5 hPa, yield 98%).

The thus obtained 3-methylbutyl glycidyl ether (100 g), acetone (200 ml) and a 3% sulfuric acid aqueous solution (100 ml) were refluxed for 2 hours. Then, after concentration at 50° C./26 hPa, toluene (200 ml) was added to the residue and the resulting mixture was washed with a 3% sodium hydroxide aqueous solution (170 g). The mixture was further washed with saturated brine (150 g) three times and concentrated, and the concentrate was purified by distillation to give 3-methylbutoxypropane-1,2-diol (63 g) (bp: 115–116° C./2.6 hPa).

SYNTHESIS EXAMPLE 2

(Synthesis of 2-ethylhexyloxypropane-1,2-diol)

From 2-ethylhexyl glycidyl ether (manufactured by Tokyo Kasei Kogyo Co. Ltd.) (100 g), 2-ethylhexyloxypropane-1,2-diol (80 g) (bp: 115° C./1.1 hPa) was synthesized in a manner similar to Synthesis Example 1.

EXAMPLE 1 AND COMPARATIVE EXAMPLES 1 TO 3

According to the formulations shown in the following Table 1, fragrance compositions of Example 1 and Comparative Examples 1 to 3 were prepared.

TABLE 1

| Ingredient | Example 1 | Comparative Example 1 | Comparative Example 2 | Comparative Example 3 |
| --- | --- | --- | --- | --- |
| 1-Decanal | 2.0 (g) | 2.0 (g) | 2.0 (g) | 2.0 (g) |
| Citral | 5.0 | 5.0 | 5.0 | 5.0 |
| Dihydromyrcenol | 5.0 | 5.0 | 5.0 | 5.0 |
| Hexamethylhexahydrocyclopentabenzopyran | 15.0 | 15.0 | 15.0 | 15.0 |
| Geranylnitrile | 3.0 | 3.0 | 3.0 | 3.0 |
| Hexylcinnamic aldehyde | 10.0 | 10. | 10. | 10.0 |
| Lemon oil | 30.0 | 30.0 | 30.0 | 30.0 |
| Linalool | 10.0 | 10.0 | 10.0 | 10.0 |
| Orange oil | 15.0 | 15.0 | 15.0 | 15.0 |
| Terpineol | 5.0 | 5.0 | 5.0 | 5.0 |
| 3-Methylbutoxypropane-1,2-diol | 10.0 | — | — | — |
| Dipropylene glycol | — | 10.0 | — | — |
| Triethyl citrate | — | — | 10.0 | — |

With regard to Example 1 and Comparative Examples 1 to 3, fragrance diffusivity and long-lasting property of fragrance of the fragrance compositions were evaluated in accordance with the following "test method for fragrance diffusivity and long-lasting property of fragrance". The results are shown in Tables 2 and 3.

(Test Method for Fragrance Diffusivity and Long-lasting Property of Fragrance)

A fragrance composition (about 10.0 mg) was measured out on a filter paper laid on the bottom of a wide-mouthed bottle having a diameter of 40 mm and a height of 50 mm. The bottle was closed, and then allowed to stand for 30 minutes to prepare an evaluation sample. The fragrance intensity immediately after the bottle was opened was evaluated as "fragrance diffusivity". The fragrance intensity after when about 5 hours with the bottle open to the air was evaluated as "long-lasting property of fragrance".

The evaluation was made three times by 10 fragrance expert panelists who each had over 5 years in the fragrance art (30 panelists in total), and was conducted in a relative manner on-the composition of Example 1, of Comparative Example 1 and the Comparative Example 2 in comparison with or relative to Comparative Example 3. Specifically, with regard to "fragrance diffusivity", the number of the panelists who felt the highest fragrance diffusivity was exhibited by each individual composition of Example 1, Comparative Example 1 and Comparative Example 2 relative to Comparative Example 3 was totaled, and the "fragrance diffusivity" evaluation was given by showing the total number of panelists that gave which Example or Comparative Example the highest fragrance diffusivity. With regard to "long-lasting property of fragrance", the number of the panelists who felt the highest long-lasting property of fragrance by the particular composition of Example 1, Comparative Example 1 and Comparative Example 2 relative to Comparative Example 3 was summarized, and the evaluation of "long-lasting property of fragrance" was given by showing the total number of panelists that selected on each Example or Comparative Example Composition as having the highest "long-lasting property of fragrance".

TABLE 2

Results of fragrance diffusivity test

|  | Example 1 | Comparative Example 1 | Comparative Example 2 | No difference felt |
|---|---|---|---|---|
| Number of experts | 15 | 6 | 6 | 7 |

TABLE 3

Results of test of long-lasting property of fragrance

|  | Example 1 | Comparative Example 1 | Comparative Example 2 | No difference felt |
|---|---|---|---|---|
| Number of experts | 21 | 4 | 5 | 4 |

As is apparent from the above Tables 2 and 3, the glyceryl ether derivative represented by the general formula (I) for use in the present invention exhibited excellent results in both fragrance diffusivity and long-lasting property of fragrance on a blended fragrance as compared with dipropylene glycol and triethyl citrate which have been hitherto employed as fixatives or fragrance-note improving agents.

EXAMPLE 2 AND COMPARATIVE EXAMPLE 4

(Effect Test on Bath Composition)

As shown in the following Table 4, a bath composition which contains anhydrous sulfate (68.45 g), sodium hydrogen carbonate (30.00 g), silicic anhydride (0.05 g) and coloring matter (0.05 g) was provided with 1.00% of the blended fragrance of Example 1 or Comparative Example 1, whereby the bath compositions of Example 2 and Comparative Example 4 were prepared, each in an amount of 100 g.

TABLE 4

Formulations of bath compositions

| Ingredient | Example 2 | Comparative Example 4 |
|---|---|---|
| Anhydrous sodium sulfate | 68.45 (g) | 68.45 (g) |
| Sodium hydrogen carbonate | 30.00 | 30.00 |
| Silicic anhydride | 0.50 | 0.50 |
| Coloring matter | 0.05 | 0.05 |
| Blended fragrance of Example 1 | 1.00 | — |
| Blended fragrance of Comparative Example 1 | — | 1.00 |
| Total | 100.00 | 100.00 |

Then, 20 g of each of the bath compositions of Example 2 and Comparative Example 4 was dissolved in 180 liters of hot water having a temperature of from 40 to 42° C. The fragrance intensity immediately after the dissolution ("fragrance diffusivity") and the fragrance intensity 30 minutes after dissolution ("long-lasting property of fragrance") were comparatively evaluated by expert panelists. The evaluation was made three times by 10 fragrance expert panelists who each had over 5 years experienced in the fragrance art (30 panelists in total). The results of the number of panelists who felt high "fragrance diffusivity" or strong "long-lasting property of fragrance" for each Example are shown in Tables 5 and 6 for each Example.

TABLE 5

Results of fragrance diffusivity test

|  | Example 2 | Comparative Example 4 | No difference felt |
|---|---|---|---|
| Number of experts | 18 | 6 | 6 |

TABLE 6

Results of test of long-lasting property of fragrance

|  | Example 2 | Comparative Example 4 | No difference felt |
|---|---|---|---|
| Number of experts | 21 | 4 | 5 |

As is apparent from Tables 5 and 6, the bath composition comprising the fragrance composition of the present invention exhibited excellent results in both fragrance diffusivity and long-lasting property of fragrance as compared with the bath composition containing dipropylene glycol which has hitherto been known as a fixative or a fragrance-note improving agent.

EXAMPLE 3 AND COMPARATIVE EXAMPLE 5

(Effect Test on Eau De Cologne)

According to the formulations shown in the following Table 7, the fragrance compositions of Example 3 and Comparative Example 5 were prepared.

TABLE 7

| Ingredient | Example 3 | Comparative Example 5 |
|---|---|---|
| Bergamot oil | 11.0 (g) | 11.0 (g) |
| cis-3-Hexenyl salicylate | 2.0 | 2.0 |
| Dihydromyrcenol | 10.0 | 10.0 |
| Ethyl linalool | 2.0 | 2.0 |
| Methyl dihydrojasmonate | 25.0 | 25.0 |
| Helional | 3.0 | 3.0 |
| Lemon oil | 5.0 | 5.0 |
| Linalyl acetate | 16.0 | 16.0 |
| Ethylene brassylate | 18.0 | 18.0 |
| Phenethyl alcohol | 8.0 | 8.0 |
| 2-Ethylhexyloxypropane-1,2-diol | 5.0 | — |
| p-Menthane-3,8-diol | — | 5.0 |

EXAMPLE 4 AND COMPARATIVE EXAMPLE 6

Eau De Colognes (95% ethanol solution) of Example 4 and Comparative Example 6 were prepared, each in an amount of 100 g, by adding 5% of the fragrance compositions of the Example 3 and Comparative Example 5, respectively. A proper amount of each Eau De Cologne was sprayed onto the inner side of the right and left forearms of each panelist through an atomizer. Fragrance diffusivity immediately after spraying and long-lasting property of fragrance after about 4 hours had passed from the spraying were evaluated. The evaluation was made by 10 fragrance expert panelists who each had experienced over 5 years experienced in the fragrance art. The number of the panelists who felt high fragrance diffusivity or strong long-lasting property of fragrance are shown in Tables 7 and 8.

TABLE 8

Results of fragrance diffusivity test

| | Example 4 | Comparative Example 6 | No difference felt |
|---|---|---|---|
| Number of experts | 5 | 3 | 2 |

TABLE 9

Results of test of long-lasting property of fragrance

| | Example 4 | Comparative Example 6 | No difference felt |
|---|---|---|---|
| Number of experts | 7 | 2 | 1 |

As is apparent from the above Tables 8 and 9, the Eau De Cologne containing the fragrance composition of the present invention exhibited excellent results, particularly in long-lasting property of fragrance, as compared with the Eau De Cologne containing p-menthane-3,8-diol, a known fixative.

EXAMPLE 5 AND COMPARATIVE EXAMPLE 7

According to the formulations shown in the following Table 10, the fragrance compositions of Example 5 and Comparative Example 7 were prepared.

TABLE 10

| Ingredient | Example 5 | Comparative Example 7 |
|---|---|---|
| Apple base | 10.0 (g) | 10.0 (g) |
| Bergamot oil | 16.0 | 16.0 |
| Ethyl acetoacetate | 5.0 | 5.0 |
| Methyl dihydrojasmonate | 25.0 | 25.0 |
| Laurinal | 3.0 | 3.0 |
| Levosandol ® | 4.0 | 4.0 |
| Orange oil | 8.0 | 8.0 |
| 10-Oxa-16-hexadecanolide | 10.0 | 10.0 |
| Phenoxanol | 6.0 | 6.0 |
| Styrallyl acetate | 3.0 | 3.0 |
| Ethyl 2,2,6-trimethylcyclohexane-carboxylate | 10.0 | 10.0 |
| 2-Ethylhexyloxypropane-1,2-diol | 20.0 | — |
| Dipropylene glycol | — | 20.0 |

EXAMPLE 6 AND COMPARATIVE EXAMPLE 8

(Effect Test on Shampoo)

According to the formulation in the following Table 11, shampoos of Example 6 and Comparative Example 8 which contained 0.50% of the fragrance compositions of the above Example 5 and Comparative Example 7, respectively, were prepared, each in an amount of 100 g.

TABLE 11

Formulation of shampoo

| Ingredient | Weight (g) |
|---|---|
| Sodium polyoxyethylene-lauryl-ether-sulfate | 14.00 |
| Lauric acid amide propyl betain | 4.00 |
| Diethanolamide of coconut oil fatty acid | 3.00 |
| Cationated cellulose | 0.50 |
| Ethylene glycol distearate | 1.00 |
| Paraoxybenzoic acid ester | 0.25 |
| Citric acid | Proper amount |
| Fragrance composition | 0.50 |
| Purified water | Balance |
| Total | 100.00 |

Using the shampoos of Example 6 and Comparative Example 8, "fragrance diffusivity" and "long-lasting property of fragrance" of the shampoos were comparatively evaluated by the following method. The evaluation was made three times by 10 fragrance expert panelists who each had over 5 years experienced (30 panelists in total) in the fragrance art. The number of the panelists who felt high fragrance diffusivity or strong long-lasting property of fragrance was totaled for each shampoo. The results are shown in Tables 12 and 13.

(Evaluation Method)

Five grams of a tress of hair (human hair) was treated (shampooed) with 2.5 g of each shampoo in 5 ml of hot water (40° C.) for 1 minute, rinsed with 1,000 ml of hot water (40° C.), dried with a towel, and then fixed to and allowed to stand on an aluminum foil to prepare an evaluation sample. The fragrance diffusivity immediately after the fixing on the foil and the long-lasting property of fragrance after about 5 hours had passed at room temperature were evaluated.

TABLE 12

Results of fragrance diffusivity test on shampoos

|  | Example 6 | Comparative Example 8 | No difference felt |
|---|---|---|---|
| Number of experts | 15 | 7 | 8 |

TABLE 13

Results of test of long-lasting property of fragrance on shampoos

|  | Example 6 | Comparative Example 8 | No difference felt |
|---|---|---|---|
| Number of experts | 22 | 5 | 3 |

EXAMPLE 7 AND COMPARATIVE EXAMPLE 9

(Effect Test on Conditioner)

According to the formulation shown in the following Table 14, the conditioners of Example 7 and Comparative Example 9 which contained 0.50% of the fragrance compositions of the above Example 5 and Comparative Example 7, respectively, were prepared, each in an amount of 100 g.

TABLE 14

Formulation of conditioner

| Ingredient | Weight (g) |
|---|---|
| Stearyltrimethylammonium chloride | 0.50 |
| Distearyldimethylammonium chloride | 1.50 |
| Jojoba oil | 2.50 |
| Cetanol | 4.50 |
| Liquid lanolin | 2.00 |
| Polyoxyethylene stearyl ether | 1.50 |
| Concentrated glycerin | 7.00 |
| Paraoxybenzoic acid ester | 0.25 |
| Sodium hydroxide | Proper amount |
| Citric acid | Proper amount |
| Fragrance | 0.50 |
| Purified water | Balance |
| Total | 100.00 |

Using the conditioners of Example 7 and Comparative Example 9, "fragrance diffusivity" and "long-lasting property of fragrance" of the conditioners were comparatively evaluated by the following method. The evaluation was made three times by 10 fragrance expert panelists each who had over 5 years experienced (30 panelists in total) in the fragrance art. The number of the panelists who felt high fragrance diffusivity or strong long-lasting property of each fragrance was totaled. The results were shown in Tables 15 and 16.

(Evaluation Method)

Five grams of a tress of hair (human hair) was treated with 5.0 g of each conditioner in 5 ml of hot water (40° C.) for 1 minute, rinsed with 1,000 ml of hot water (40° C.), dried with a towel, and then fixed to and allowed to stand on an aluminum foil to prepare an evaluation sample. The fragrance diffusivity immediately after the fixing on the foil and the long-lasting property of fragrance after about 5 hours had passed at room temperature were evaluated.

TABLE 15

Results of fragrance diffusivity test on conditioners

|  | Example 7 | Comparative Example 9 | No difference felt |
|---|---|---|---|
| Number of experts | 20 | 7 | 3 |

TABLE 16

Results of test of long-lasting property of fragrance on conditioners

|  | Example 7 | Comparative Example 9 | No difference felt |
|---|---|---|---|
| Number of experts | 23 | 4 | 3 |

As is apparent from Tables 12, 13, 15 and 16, the shampoo and the conditioner containing the fragrance composition of the present invention exhibit excellent results in both fragrance diffusivity and long-lasting property of fragrance, particularly a remarkable effect on long-lasting property of fragrance, as compared with the conditioner containing a known fixative or fragrance-note improving agent.

EXAMPLE 8 AND COMPARATIVE EXAMPLES 10 And 11

(Effect Test on Shampoo)

According to the formulations shown in the following Table 17, the shampoos (each in an amount of 100 g in a usual manner) of Example 8 and Comparative Examples 10 and 11 were prepared. A floral fruity green type fragrance composition (TSP-3055® (manufactured by Takasago International Corporation)) was added in a fragrance-providing amount of 0.3% to each shampoo.

TABLE 17

Formulations of shampoos

| Ingredient | Example 8 | Comparative Example 10 | Comparative Example 11 |
|---|---|---|---|
| Sodium polyoxyethylene-lauryl-ether sulfate | 14.00 (g) | 14.00 (g) | 14.00 (g) |
| Lauric acid amide propyl betain | 4.00 | 4.00 | 4.00 |
| Diethanolamide of coconut oil fatty acid | 3.00 | 3.00 | 3.00 |
| Cationated cellulose | 0.50 | 0.50 | 0.50 |
| Ethylene glycol distearate | 1.00 | 1.00 | 1.00 |
| Paraoxybenzoic acid ester | 0.25 | 0.25 | 0.25 |
| Citric acid | Proper amount | Proper amount | Proper amount |
| 2-Ethylhexyloxypropane-1,2-diol | — | 0.03 | — |
| Fragrance composition (TSP-3055 ®) | — | 0.30 | 0.30 |

TABLE 17-continued

Formulations of shampoos

| Ingredient | Example 8 | Comparative Example 10 | Comparative Example 11 |
|---|---|---|---|
| TSP-3055 ® containing 9.1% of 2-ethylhexyloxypropane-1,2-diol | 0.39 | — | — |
| Purified water | Balance | Balance | Balance |
| Total | 100.00 | 100.00 | 100.00 |

The shampoos of Example 8 and Comparative Examples 10 and 11 were evaluated for "fragrance diffusivity" and "long-lasting property of fragrance" in the same manner as in Example 6 and Comparative Example 8. The results are shown in Tables 18 and 19.

TABLE 18

Results of fragrance diffusivity test on shampoos

| | Example 8 | Comparative Example 10 | Comparative Example 11 |
|---|---|---|---|
| Number of experts | 16 | 10 | 4 |

TABLE 19

Results of test of long-lasting property of fragrance on shampoos

| | Example 8 | Comparative Example 10 | Comparative Example 11 |
|---|---|---|---|
| Number of experts | 20 | 7 | 3 |

EXAMPLE 9 AND COMPARATIVE EXAMPLES 12 AND 13

(Effect Test on Conditioner)

According to the formulations shown in the following Table 20, the conditioners of Example 9 and Comparative Examples 12 and 13 were prepared in a conventional manner. To each conditioner a floral fruity green type fragrance composition (TSP-3055® (manufactured by Takasago International Corporation)) was added in a fragrance-providing rate of 0.3% per 100 μg of conditioner.

TABLE 20

Formulations of conditioners

| Ingredient | Example 9 | Comparative Example 12 | Comparative Example 13 |
|---|---|---|---|
| Stearyltrimethylammonium chloride | 0.50 (g) | 0.50 (g) | 0.50 (g) |
| Distearyldimethylammonium chloride | 1.50 | 1.50 | 1.50 |
| Jojoba oil | 2.50 | 2.50 | 2.50 |
| Cetanol | 4.50 | 4.50 | 4.50 |
| Liquid lanolin | 2.00 | 2.00 | 2.00 |
| Polyoxyethylene stearyl ether | 1.50 | 1.50 | 1.50 |
| Concentrated glycerin | 7.00 | 7.00 | 7.00 |
| Paraoxybenzoic acid ester | 0.25 | 0.25 | 0.25 |
| Sodium hydroxide | Proper amount | Proper amount | Proper amount |
| Citric acid | Proper amount | Proper amount | Proper amount |
| 2-Ethylhexyloxypropane-1,2-diol | — | 0.03 | — |
| Fragrance composition (TSP-3055®) | — | 0.30 | 0.30 |
| TSP-3055 ® containing 9.1% of 2-ethylhexyloxypropane-1,2-diol | 0.39 | — | — |
| Purified water | Balance | Balance | Balance |
| Total | 100.00 | 100.00 | 100.00 |

The conditioners of Example 9 and Comparative Examples 12 and 13 were evaluated for "fragrance diffusivity" and "long-lasting property of fragrance" in the same manner as in Example 7 and Comparative Example 9. The results are shown in Tables 21 and 22.

TABLE 21

Results of fragrance diffusivity test on conditioner

| | Example 9 | Comparative Example 12 | Comparative Example 13 |
|---|---|---|---|
| Number of experts | 13 | 10 | 7 |

TABLE 22

Results of test of long-lasting property of fragrance on conditioner

| | Example 9 | Comparative Example 12 | Comparative Example 13 |
|---|---|---|---|
| Number of experts | 19 | 8 | 3 |

As is apparent from Tables 18, 19, 21 and 22, the shampoo and conditioner of Examples 8 and 9 containing the fragrance composition of the present invention exhibited excellent results in both fragrance diffusivity and long-lasting property of fragrance, particularly a remarkable effect on long-lasting property of fragrance. Moreover, from a comparison between Examples 8 and 9 and Comparative Examples 10 and 12 in Tables 18, 19, 21 and 22, it is clear that a high fragrance note-improving effect was only obtained in the case that the glyceryl ether derivative was present in the fragrance composition, even when the compositions were otherwise the same.

EXAMPLES 10 TO 13 AND COMPARATIVE EXAMPLES 14 AND 15

Conditioners of Examples 10 to 13 and Comparative Examples 14 and 15 were prepared with the same formulation as the formulation of the fragrance composition of Example 9 in Table 20 with the exception that the 2-ethylhexyloxypropane-1,2-diol was replaced with n-butoxypropane-1,2-diol (Example 10), 3-methylbutoxypropane-1,2-diol (Example 11), n-octyloxypropane-1,2-diol (Example 12), 4-methylphenyloxypropane-1,2-diol (Example 13), ethoxypropane-1,2-diol (Comparative Example 14) or 9-octadecenyloxypropane-1,2-diol (Comparative Example 15), respectively.

The conditioners of Examples 10 to 13 and Comparative Examples 14 and 15, and additionally the conditioner of Example 9 were evaluated for "fragrance diffusivity" and "long-lasting property of fragrance" after being applied to a blotter. Evaluation was in comparison to above Comparative Example 13 (a conditioner wherein additive-free TSP-3055 was used as a fragrance composition). The evaluation was made by 10 fragrance expert panelists who had over 5 years experienced in the fragrance art. An evaluation score was determined according to the following seven-stage criteria. The rankings in Table 23 are an average of the rankings from each of the 10 panelists on each conditioner.

(Evaluation Score)
7: Very high as compared with Comparative Example 13
6: High as compared with Comparative Example 13
5: Slightly high as compared with Comparative Example 13
4: Equal to Comparative Example 13
3: Example 13 is slightly higher
2: Example 13 is higher
1: Example 13 is clearly higher

TABLE 23

|  | Fragrance diffusivity | Long-lasting property of fragrance |
| --- | --- | --- |
| Example 9 | 5.8 | 6.2 |
| Example 10 | 4.5 | 5.3 |
| Example 11 | 4.8 | 5.4 |
| Example 12 | 4.8 | 5.6 |
| Example 13 | 5.3 | 5.7 |
| Comparative Example 14 | 3.6 | 2.7 |
| Comparative Example 15 | 3.2 | 3.8 |

From the evaluation scores of Examples 9 and 12, it is seen that $R^1$ having a branched chain in general formula (I) exhibits a higher effect and a substituent having an aromatic ring also exhibits a high effect (Example 13). Furthermore, from a comparison with the Comparative Examples, it is seen that the number of carbon atoms of $R^1$ has a very great influence on fragrance properties.

EXAMPLE 14

According to the formulation shown in the following Table 24, 100 g of a softener was prepared in a conventional manner using a floral woody musky fragrance composition (TIC 2002® (manufactured by Takasago International Corporation)). The TIC 2002® contained 5% of 2-ethylhexyloxypropane-1,2-diol as a fragrance component.

TABLE 24

| Formulation of softener | |
| --- | --- |
| Ingredient | Weight (g) |
| Dehicoat AU-56 (manufactured by Kognis) | 15.00 |
| Methylparaben | 0.20 |
| 10% sodium hydroxide | 0.50 |
| Magnesium chloride | 0.20 |
| Floral woody musky fragrance composition TIC 2002 ® (manufactured by Takasago | 0.50 |

TABLE 24-continued

| Formulation of softener | |
| --- | --- |
| Ingredient | Weight (g) |
| International Corporation) containing 5% of 2-ethylhexyloxypropane-1,2-diol | |
| Purified water | Balance |
| Total | 100.00 |

EXAMPLE 15

According to the formulation shown in the following Table 25, 100 g of an emollient cream was prepared in a conventional manner using a floral powdery fragrance composition (BF-6370-C® (manufactured by Takasago International Corporation)) containing 10% of 3-methylbutoxypropane-1,2-diol as a fragrance component.

TABLE 25

| Formulation of emollient cream | |
| --- | --- |
| Ingredient | Weight (g) |
| Hardened oil | 6.00 |
| Stearic acid | 3.00 |
| Cetanol | 4.00 |
| Squalane | 2.00 |
| Neopentyl glycol dicaprate | 8.00 |
| Polyoxyethylene sorbitan monostearate (20 E.O.) | 4.00 |
| Lipophilic glycerin monostearate | 2.30 |
| Stearoyl-N-methyltaurine sodium | 1.70 |
| 1,3-Butylene glycol | 7.00 |
| Concentrated glycerin | 3.00 |
| Paraoxybenzoic acid ester | 0.25 |
| Floral powdery fragrance composition BF-6370-C ® (manufactured by Takasago International Corporation) containing 10% of 3-methylbutoxypropane-1,2-diol | 0.05 |
| Purified water | Balance |
| Total | 100.00 |

EXAMPLE 16

According to the formulation shown in the following Table 26, 100 g of an emollient cream was prepared in a conventional manner using a floral powdery fragrance composition (BF-6372® (manufactured by Takasago International Corporation)) containing 3% of 2-ethylhexyloxypropane-1,2-diol as a fragrance component.

TABLE 26

| Formulation of emollient milk | |
| --- | --- |
| Ingredient | Weight (g) |
| Stearic acid | 1.00 |
| Cholesteryl isostearate | 2.00 |
| Jojoba oil | 4.00 |
| Squalane | 8.00 |
| Sorbitan sesquioleate | 0.80 |
| Polyoxyethylene sorbitan monostearate (20 E.O.) | 1.20 |
| 1,3-Butylene glycol | 5.00 |
| Paraoxybenzoic acid ester | 0.25 |
| L-arginine | 0.40 |

TABLE 26-continued

Formulation of emollient milk

| Ingredient | Weight (g) |
|---|---|
| Carboxyvinyl polymer | 0.20 |
| Floral powdery fragrance composition BF-6372 ® (manufactured by Takasago International Corporation) containing 3% of 2-ethylhexyloxypropane-1,2-diol | 0.10 |
| l-Menthol | 0.20 |
| Purified water | Balance |
| Total | 100.00 |

EXAMPLE 17

According to the formulation shown in the following Table 27, 100 g of a hair rinse was prepared in a conventional manner using a fruity green floral fragrance composition (BF-6032® (manufactured by Takasago International Corporation)) containing 5% of 2-ethylhexyloxypropane-1,2-diol as a fragrance component.

TABLE 27

Formulation of hair rinse

| Ingredient | Weight (g) |
|---|---|
| Stearyltrimethylammonium chloride | 1.00 |
| Cetanol | 3.00 |
| Methyl polysiloxane | 1.00 |
| Polyoxyethylene stearyl ether | 1.00 |
| Propylene glycol | 5.00 |
| Paraoxybenzoic acid ester | 0.25 |
| Sodium hydroxide | Proper amount |
| Citric acid | Proper amount |
| Fruity green floral fragrance composition BF-6032 (manufactured by Takasago International Corporation) containing 5% of 2-ethylhexyloxypropane-1,2-diol | 0.50 |
| l-Menthol | 0.20 |
| Purified water | Balance |
| Total | 100.00 |

EXAMPLE 18

According to the formulation shown in the following Table 28, 100 g of a liquid bath composition was prepared in a conventional manner using a lemon fragrance composition (JC-005A® (manufactured by Takasago International Corporation)) containing 10% of 2-ethylhexyloxypropane-1,2-diol as a fragrance component.

TABLE 28

Formulation of liquid bath composition

| Ingredient | Weight (g) |
|---|---|
| Dipropylene glycol | 50.00 |
| 1,3-Butylene glycol | 10.00 |
| Paraoxybenzoic acid ester | 0.20 |
| l-Menthol | 0.30 |
| Lemon fragrance composition JC-005A ® (manufactured by Takasago International Corporation) containing 10% of 2- | 1.00 |

TABLE 28-continued

Formulation of liquid bath composition

| Ingredient | Weight (g) |
|---|---|
| ethylhexyloxypropane-1,2-diol | |
| Purified water | Balance |
| Total | 100.00 |

The products of the above Examples 14 to 18 were satisfactory in both fragrance diffusivity and long-lasting property of fragrance.

As described above, the incorporation of the glyceryl ether derivative represented by general formula (I) into a fragrance composition enables a remarkable enhancement of fragrance diffusivity and long-lasting property of fragrance without changing the fragrance note of a known or well-known fragrance as compared with hitherto known fixatives and fragrance note-improving agents. Thus, according to the present invention, it is possible to obtain a fragrance composition having desired fragrance properties and a remarkably high fixative property.

Moreover, the effects are the same in a diverse number of different products containing the fragrance composition of the present invention. Accordingly, products such as cosmetics, toiletry products, bath compositions and pharmaceuticals having desired fragrance properties and having high fragrance diffusivity and long-lasting property of fragrance can be obtained using the fragrance composition of the present invention.

While the invention has been described in detail and with reference to specific embodiments thereof, it will be apparent to one skilled in the art that various changes and modifications can be made therein without departing from the scope thereof.

This application is based on Japanese patent application No. 2002-045985 filed Feb. 22, 2002, the entire contents thereof being hereby incorporated by reference.

What is claimed is:

1. A method of enhancing fragrance property, fragrance diffusivity and fixative effect of a fragrance composition, which comprises incorporating into the fragrance composition a glyceryl ether derivative represented by the general formula:

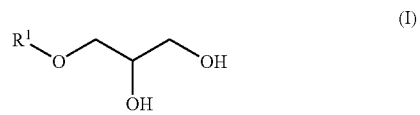

(I)

wherein $R^1$ represents a 2-ethylhexyl group.

2. The method according to claim 1, wherein the glyceryl ether derivative is present in an amount of 0.1 to 90% by weight relative to the total amount of the fragrance composition including the glyceryl ether.

3. The method according to claim 2, wherein the glyceryl ether derivative is present in an amount of 0.5 to 30% by weight relative to the total amount of the fragrance composition including the glyceryl ether derivative.

4. The method of claim 1, wherein said glyceryl ether derivative is a colorless and substantially odorless oily substance which, when incorporated into the aroma substances, enhances the fragrance property, fragrance diffusivity and fixative effect of the fragrance composition without changing the fragrance note of the fragrance composition.

* * * * *